(12) United States Patent
Chevolleau et al.

(10) Patent No.: US 12,370,311 B2
(45) Date of Patent: Jul. 29, 2025

(54) METHOD FOR REDUCING AN AMOUNT OF SUBVISIBLE PARTICLES IN A PHARMACEUTICAL COMPOSITION

(71) Applicant: Becton Dickinson France, Le Pont de Claix (FR)

(72) Inventors: Tzvetelina Chevolleau, Saint Egreve (FR); Benoit Fremon, Saint Martin d'Uriage (FR); Jean-Bernard Hamel, Saint Cassien (FR); Sébastien Jouffray, Saint Martin d'Uriage (FR)

(73) Assignee: Becton Dickinson France, Le Pont de Claix (FR)

( * ) Notice: Subject to any disclaimer, the term of this patent is extended or adjusted under 35 U.S.C. 154(b) by 0 days.

(21) Appl. No.: 18/122,430

(22) Filed: Mar. 16, 2023

(65) Prior Publication Data
US 2023/0218830 A1    Jul. 13, 2023

Related U.S. Application Data

(63) Continuation of application No. 16/316,736, filed as application No. PCT/EP2017/067368 on Jul. 11, 2017, now Pat. No. 11,628,257.

(30) Foreign Application Priority Data

Jul. 11, 2016   (EP) .................................. 16305874

(51) Int. Cl.
*A61M 5/31*   (2006.01)
*A61M 5/315*   (2006.01)

(52) U.S. Cl.
CPC ........ *A61M 5/3134* (2013.01); *A61M 5/3129* (2013.01); *A61M 2005/3117* (2013.01);
(Continued)

(58) Field of Classification Search
CPC .. A61M 5/282; A61M 5/3129; A61M 5/3134; B05C 17/00576
See application file for complete search history.

(56) References Cited

U.S. PATENT DOCUMENTS 4,022,206 A * 5/1977 Hilleman ............... A61M 5/282
                                                    604/212
5,456,940 A   10/1995 Funderburk
(Continued)

FOREIGN PATENT DOCUMENTS

JP   H7280177 A   10/1995
JP   2005160888 A   6/2005
(Continued)

*Primary Examiner* — Dah-Wei D. Yuan
*Assistant Examiner* — Andrew J Bowman
(74) *Attorney, Agent, or Firm* — The Webb Law Firm

(57) ABSTRACT

The invention relates to a method for reducing an amount of sub visible particles in a pharmaceutical composition contained in a medical injection device comprising a container (1) including a barrel (10) lubricated with a lubricant coating (2) in contact with the pharmaceutical composition, and a stopper (14) in sliding engagement within the barrel (10), the container comprising a region (130, 121, 123) extending distally from the distal end (100) of the barrel which is not accessible to the stopper. During formation of said lubricant coating (2) on the inner wall of the barrel, the method comprises limiting lubricant from being deposited into said region (130, 121, 123) extending distally from the distal end (100) of the barrel.

3 Claims, 3 Drawing Sheets

(52) U.S. Cl.
CPC ............ *A61M 2005/3131* (2013.01); *A61M 2005/31516* (2013.01); *A61M 2205/0222* (2013.01); *A61M 2205/0238* (2013.01)

(56) References Cited

U.S. PATENT DOCUMENTS

| | | | |
|---|---|---|---|
| 6,296,893 | B2 | 10/2001 | Heinz et al. |
| 6,461,334 | B1 | 10/2002 | Buch-Rasmussen et al. |
| 2002/0012741 | A1* | 1/2002 | Heinz ............... B05C 17/00576 |
| | | | 427/372.2 |
| 2004/0267194 | A1* | 12/2004 | Sano ................... A61M 5/3129 |
| | | | 604/93.01 |
| 2012/0277686 | A1 | 11/2012 | Muramatsu |

FOREIGN PATENT DOCUMENTS

| | | | |
|---|---|---|---|
| JP | 2015523422 | A | 8/2015 |
| WO | 2010034004 | A1 | 3/2010 |
| WO | 2011092536 | A1 | 8/2011 |
| WO | 2013045571 | A3 | 4/2013 |
| WO | 2013167617 | A2 | 11/2013 |
| WO | 2015181173 | A1 | 12/2015 |
| WO | 2016102068 | A1 | 6/2016 |

\* cited by examiner

METHOD FOR REDUCING AN AMOUNT OF SUBVISIBLE PARTICLES IN A PHARMACEUTICAL COMPOSITION

CROSS-REFERENCE TO RELATED APPLICATIONS

This application is a continuation of U.S. patent application Ser. No. 16/316,736 filed Jul. 11, 2017, which is the United States national phase of International Application No. PCT/EP2017/067368 filed Jul. 11, 2017, and claims priority to European Patent Application No. 16305874.6 filed Jul. 11, 2016, the disclosures of which are hereby incorporated in their entirety by reference.

FIELD OF THE INVENTION

The invention relates to a method for reducing sub visible particles in a pharmaceutical composition contained in a medical injection device.

In this application, the distal end of a component or apparatus must be understood as meaning the end furthest from the hand of the user and the proximal end must be understood as meaning the end closest to the hand of the user, with reference to the injection system intended to be used with said component or apparatus. As such, in this application, the distal direction must be understood as the direction of injection with reference to the injection system, and the proximal direction is the opposite direction, i.e. the direction towards the hand of the user.

BACKGROUND OF THE INVENTION

A medical injection device such as a syringe comprises a container intended to contain a pharmaceutical composition.

The container comprises a barrel which is cylindrical with a circular cross section, a proximal end by which a user may handle the container during operation, and a distal end comprising an outlet for the pharmaceutical composition, e.g. through a needle or an intravenous (IV) line to be connected to the tip of the container. The tip of the container comprises an implantation channel for such a needle or intravenous line.

A stopper generally made of an elastomeric material is arranged in sliding engagement within the barrel.

During injection of the pharmaceutical composition into a patient's body, the stopper slides from the proximal end to the distal end of the barrel in order to push the pharmaceutical composition through the tip.

Since the tip of the container has a smaller diameter than the barrel, there is a region comprised between the distal end of the barrel and the tip of the container that is not accessible to the stopper. Thus, once the stopper has fully slid along the barrel, there remains a volume of pharmaceutical composition contained between the stopper and the proximal end of the tip. This region of the container is called "dead space". A volume of pharmaceutical composition is also contained in the implantation channel—and, if a hollow needle is inserted into the implantation channel, a volume of pharmaceutical composition is also contained in the inner space of said hollow needle.

In order to improve sliding of the stopper within the barrel, the barrel is usually lubricated with a lubricant coating, e.g. made of silicone. The coating can be deposited on the inner walls of the barrel either by spraying, dipping, etc.

In contact with the pharmaceutical composition, the lubricant coating can migrate into the filling solution under the form of lubricant droplets of various sizes (from visible to not visible to human eyes and thus called "sub visible particles").

Since such particles may be detrimental for the drug quality and/or drug stability, upper limits for amounts of sub visible particles are regulated by USP <788> and other guidance.

A change in the deposition process of the lubricant coating may generate significantly higher particles level and the Applicant had to remedy to such situation for the reasons mentioned here above.

SUMMARY OF THE INVENTION

A goal of the invention is to optimize the deposition process of the lubricant coating so as to ensure that the sub visible particles level will remain below the limit provided by the regulatory guidance.

Accordingly, the invention provides a method for reducing an amount of sub visible particles in a pharmaceutical composition contained in a medical injection device comprising a container including a barrel lubricated with a lubricant coating in contact with the pharmaceutical composition, and a stopper in sliding engagement within the barrel, the container comprising a region extending distally from the distal end of the barrel which is not accessible to the stopper, characterized in that, during formation of said lubricant coating on the inner wall of the barrel, the method comprises limiting lubricant from being deposited into said region extending distally from the distal end of the barrel.

According to an embodiment, the lubricant is sprayed onto the inner wall of the barrel by a nozzle through a proximal end of the container, the spray being configured to limit deposition of lubricant into the region extending distally from the distal end of the barrel.

According to an embodiment, the nozzle is fixed relative to the container.

According to another embodiment, the nozzle is movingly inserted into the barrel.

The method may comprise, after deposition of the lubricant, a step of annealing the lubricant coating.

Alternatively, the method may comprise, after deposition of the lubricant, a step of treating the lubricant coating with a plasma.

According to an embodiment, the formation of the lubricant coating comprises adsorbing a chemical precursor of the lubricant carried by a vector gas on the inner wall of the barrel and cross-linking the chemical precursor with a plasma.

The total amount of lubricant deposited into the region extending distally from the distal end of the barrel is advantageously less than 25 μg, preferably less than 20 μg.

The lubricant may comprise poly-(dimethylsiloxane) or an emulsion of poly-(dimethylsiloxane).

According to an embodiment, the container further comprises a tip comprising an implantation channel and a hollow needle inserted in said implantation channel, the method comprising limiting lubricant from being deposited into said implantation channel and the inner space of the hollow needle.

As a result of the above method, the medical injection device advantageously comprises:

a container intended to contain a pharmaceutical composition including a barrel lubricated with a lubricant coating intended to be in contact with the pharmaceutical composition, a stopper in sliding engagement within the barrel, the container comprising a region extending distally from the distal end of the barrel which is not accessible to the stopper, said region extending distally from the distal end of barrel containing a limited amount of the lubricant, said limited amount being less than 25 µg, preferably less than 20 µg.

The medical injection device may further comprise a pharmaceutical composition in contact with the lubricant coating in the barrel.

BRIEF DESCRIPTION OF THE DRAWINGS

Other features and advantages of the invention will be apparent from the detailed description that follows, based on the appended drawings wherein.

DETAILED DESCRIPTION OF EMBODIMENTS OF THE INVENTION

Figure 1:
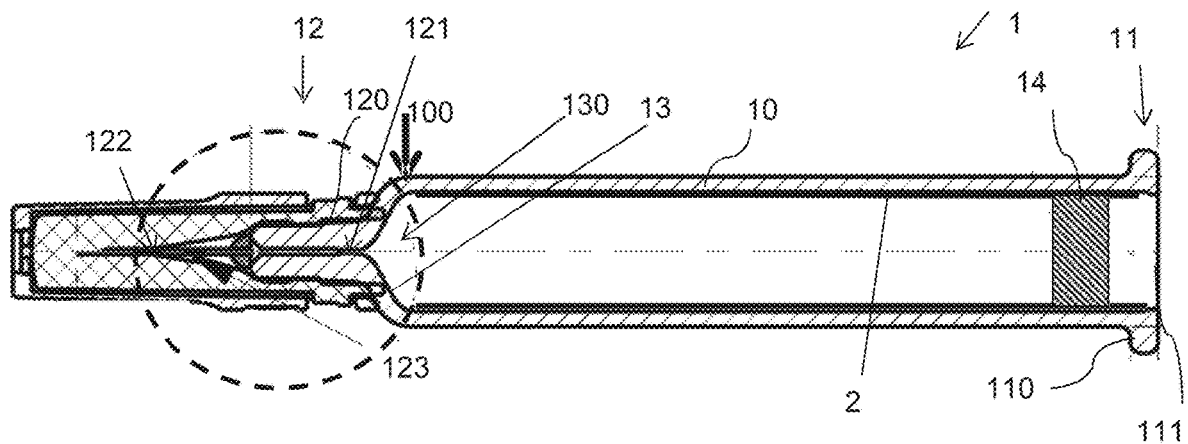
FIG. 1 is a cross sectional view of a container of a medical injection device according to an embodiment of the invention.

FIG. 1 is a cross sectional view of a container of a medical injection device according to an embodiment of the invention.

The container 1 comprises a barrel 10 which has a cylindrical shape with a circular cross section.

The proximal end 11 of the container comprises a flange 110 that allows a user to handle the container during operation of the medical injection device.

A stopper 14 is inserted into the barrel through an opening 111 of said proximal end 11.

The distal end 12 of the container comprises a tip 120.

The tip 120 may be of luer type in order to be connected to a needle hub, a cap or a catheter via an intravenous (IV) line, or may comprise a staked needle. In the non-limitative embodiment of FIG. 1, the tip comprises an implantation channel 121 into which is inserted a hollow needle 122 having an inner space 123 allowing the pharmaceutical composition to come in or out.

Since the tip 120 has a smaller diameter than the barrel 10, it is connected to the barrel by a tapered wall 13. The barrel 10 is thus defined as the part of the container that has a constant diameter adapted to the sliding motion of the stopper 4. The distal end 100 of the barrel is thus defined by the junction between the cylindrical wall inner of the barrel 10 and the tapered wall 13. The region of the container that extends distally from said distal end 100 of the barrel is not accessible to the stopper.

The region surrounded by the tapered wall 13 is the dead space 130. The implantation channel 121 extends between the distal end of the tip 120 and the dead space 130.

In the embodiment illustrated in FIG. 1, the region extending from the distal end 100 of the barrel includes the dead space 130, the implantation channel 121 and the inner space 123 of the needle. In case the medical injection device does not comprise any needle but only a channel extending through the tip, the region extending from the distal end of the barrel includes the dead space and said channel.

The container may be formed from either glass or a plastic material suitable for the intended medical use.

A lubricant coating 2 is applied to the inner wall of the barrel 10 in order to improve sliding of the stopper along the barrel.

The lubricant coating will thus be in contact with the pharmaceutical composition when the container is filled with said pharmaceutical composition.

The lubricant may be any lubricant currently used in the medical field to lubricate containers. For example, the lubricant may comprise silicone. In particular, but not restrictively, the silicone may comprise poly-(dimethylsiloxane) (PDMS). In another example, the lubricant may comprise an emulsion of poly-(dimethylsiloxane) which may subsequently be annealed to form so-called "baked silicone".

During application of said lubricant coating, care is taken not to apply lubricant to the region of the container that extends distally from the distal end of the barrel, i.e., in the embodiment illustrated in FIG. 1, into the dead space 130, the implantation channel 121 and the inner space of the needle 122 (which correspond to the region inside the circular dotted line in FIG. 1).

The following description is directed to an embodiment wherein the application of the lubricant coating is done by spraying the lubricant inside the container thanks to a nozzle. However, it is to be noted that the invention applies to any other way of applying the lubricant coating. For example, the application of the lubricant coating may be done by Plasma Enhanced Chemical Vapor Deposition (PECVD), which comprises adsorbing a chemical precursor of the lubricant carried by a vector gas on the inner wall of the barrel, and then cross-linking the chemical precursor thanks to a plasma induced by an electrode to yield a lubricant layer. In this case, the deposition of the chemical precursor is controlled such that the precursor is deposited into the barrel but not into the region that extends distally from the distal end of the barrel.

Figure 2:
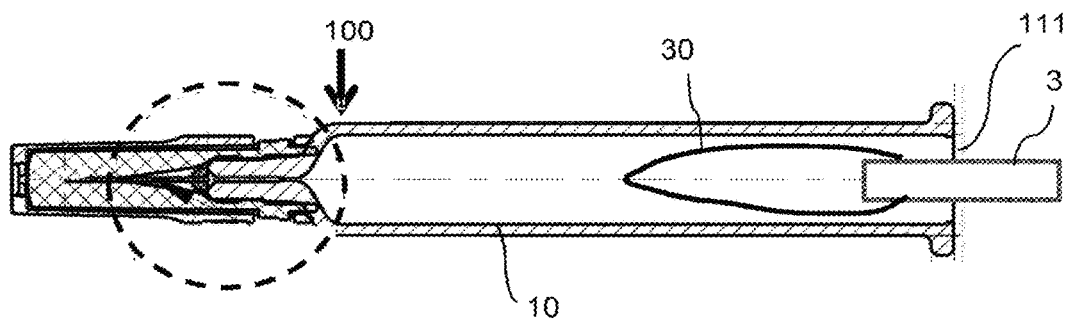
FIG. 2 schematically illustrates a spraying nozzle at the proximal opening of the barrel.

As shown in FIG. 2, a nozzle 3 is placed at the opening 111 of the proximal end of the container and is fed with lubricant, e.g. silicone oil, such that a spray 30 formed of a plurality of lubricant droplets is applied into the barrel.

Depending on the spraying technology, the nozzle may be fixed relative to the barrel (so-called "fixed nozzle") or may be moved axially in the distal direction inside the barrel (so-called "diving nozzle").

The morphology of the spray (i.e. the shape of the spray and the size of the lubricant droplets) may depend on several process parameters, including the pressure and temperature of the lubricant, which have an effect on the viscosity of the lubricant. The shape of the spray is defined in particular by the length of the spray (in the axial direction of the barrel) and by the width of the spray (in the radial direction).

Dimensional parameters of the nozzle may also have an effect onto the morphology of the spray. In particular, the size and shape of the nozzle defines a shear strain of the lubricant, which in turn influences the size and shape of the lubricant droplets.

In any case, the nozzle is placed relative to the container such that the lubricant spray does not contact the region extending distally from the distal end of the barrel. Hence, the lubricant coating is selectively deposited on the inner wall of the barrel, excluding the tapered wall connecting the barrel to the tip and more generally any space extending distally from the distal end of the barrel. However, since it may not be excluded that a slight amount of lubricant enters the dead space, the implantation channel and/or the inner space of the needle, either directly during spraying or due to migration along the walls of the container, the Applicant has defined a maximum amount of lubricant that may be introduced into the region extending distally from the distal end of the barrel without being detrimental to the level of sub visible particles generated by flushing (see FIG. 4 and the corresponding description below).

In document U.S. Pat. No. 6,296,893, the distal end section A of the inner wall of the barrel is left uncoated in order to prevent a piston from being moved back into the interior of the container; to that end, the axial dimension of said uncoated section is at least 5 or 6 mm. To the contrary, in the present invention, the lubricant is deposited onto the inner wall of the barrel until the junction with the dead space.

For a given nozzle and given process conditions, the skilled person is able to determine the morphology of the spray and thus the suitable operation to be performed on the nozzle so as to avoid applying lubricant into the region extending distally from the distal end of the barrel.

If necessary, after performing the lubrication step, the skilled person may check that no lubricant—or a sufficiently small amount of lubricant—has been deposited in the excluded region by cutting the medical container at the junction between the barrel and the tapered wall so as to keep the portion comprised between said junction and the tip, and by extracting any lubricant present in this portion of the container. If some lubricant is extracted, the skilled person may then adjust the process parameters until not finding any lubricant—or an amount less than a given threshold—in said portion of the container.

The extraction procedure of the lubricant may be carried out as follows. In the example, we consider 1 mlL Long (mlL) syringes and 2.25 ml syringes coated with silicone.

Each syringe is filled with MIBK: 1.6 ml of MIBK (Methyl Isobutyl Ketone) in 1 mlL syringes and 3.1 ml of MIBK in 2.25 ml syringes. The silicone is extracted with ultrasonic bath at 40° C. during 15 minutes. The MIBK is collected and the total volume of sample is completed to 3 ml by adding 1.4 ml of MIBK for the 1 mlL syringes and the silicone oil is directly titrated by F-AAS (Atomic absorption spectroscopy, flame mode) as described below.

Atomic absorption spectroscopy (AAS) is an elemental analysis technique. It allows quantifying an element of interest contained in a sample. The concentration of element is deduced from the measurement of the light absorption by the remaining atoms of the element to the ground state when illuminated by a suitable light source. Measuring the light intensity is performed at a specific wavelength of the analyzed element. A calibration curve can be drawn from the obtain signal, correlating signal intensity to concentration. In the current case, the element assayed is silicon (Si) in order to determine the amount of silicone oil containing in samples.

The AAS spectroscope used is a Perkin Elmer AA800 with a Graphite Furnace mode (GF-AAS) to quantify small quantities of elements and a flame mode (F-AAS) to quantify larger quantities.

Other methods could be used, e.g. infrared spectroscopy, gas chromatography mass spectrometry (GCMS), or flame ionization detection (GC-FID).

In addition to GC, other techniques can be used to identify and/or quantify the lowest molecular weight species present in silicone polymers; for example, gel permeation chromatography (GPC) or supercritical fluid chromatography (SFC).

It is to be noted that when prior art documents, e.g. WO 2013/045571, mention a coverage percentage of the lubricant coating measured by RapID, said coverage is measured relative to the barrel only and does not take into account the region extending distally from the distal end of the barrel, which was not considered as being of any interest in the prior art.

The container may be a prefilled container, i.e. a container filled with a pharmaceutical composition intended to be stored for a certain time before being injected into a patient.

Otherwise, the medical injection device may be stored empty before use. In such case, the medical injection device may for example be used for expelling a pharmaceutical composition from a reservoir and for subsequently injecting it into a patient or transferring it to another reservoir.

The invention may apply to both situations, since turbulence in the region extending distally from the distal end of the barrel, e.g. the dead space, the implantation channel and/or the needle inner space, due to actuation of the stopper may occur in both cases.

After deposition of the lubricant coating into the barrel, the coating may be subjected to any treatment currently used in the field, e.g. an annealing and/or a plasma treatment, in particular intended to reticulate the lubricant.

Figure 3:
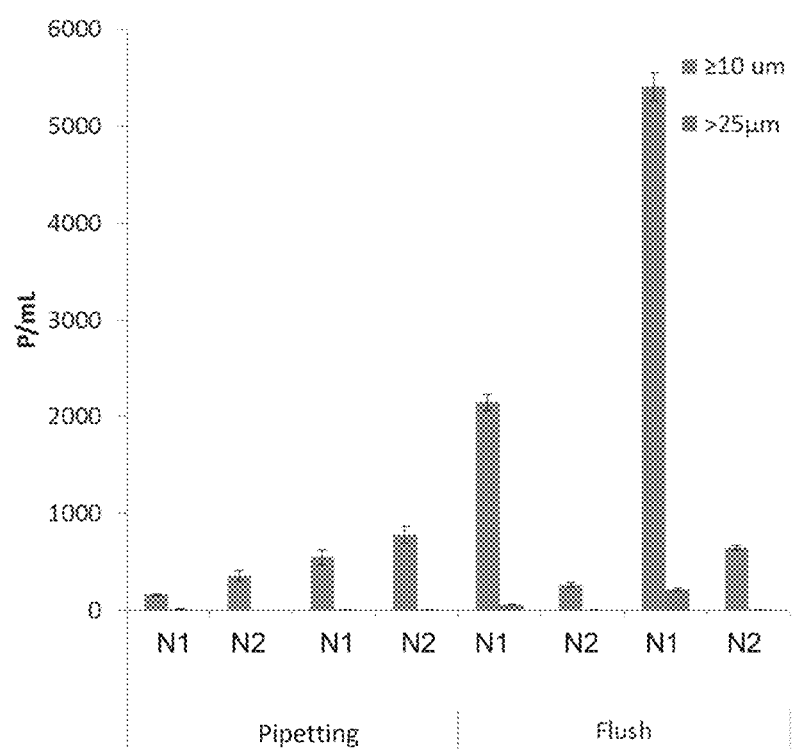
FIG. 3 shows the effect of turbulence occurring in the dead space, the implantation channel and the inner space of the needle of a medical injection device on the sub visible particles generated in the pharmaceutical composition.

FIG. 3 shows experimental results of the level of sub visible particles greater than 10 μm (left-hand bars) and greater than 25 μm (right-hand bars) (in number of particles/ml) depending on the nozzle used and on the method implemented. In this case, the lubricant is silicone (PDMS).

All syringes were filled with 0.02% Polysorbate in polyphosphate buffer, stoppered and agitated for 48 h. For each technique (pipetting or flush), the filling content is decreasing from the left to the right from 1 ml to 0.5 ml, each successive pair N1, N2 having the same filling content (N2 correspond to syringes according to the invention, with a limited silicone content (e.g. less than 20 μg) in the tip/dead space region; N1 correspond to defective syringes with a high silicone content (e.g. greater than 60 μg) in the tip/dead space region).

Pipetting results were measured after stopper removal, pipetting of the solution and analysis of individual syringes by Micro Flow Imaging (left part of the graph): no significant difference is observable between the two types of syringes.

Flush results were obtained from syringes whose content was expelled through the needle by applying compression on the stopper and syringe content was analyzed by Light Obscuration. N1 syringes show a much higher particle count for particles >10 μm than the N2 reference syringes.

For sub visible particles, the most suitable counting methods are based on optical technologies: a first method is Light Obscuration (LO), a second method is Micro Flow Imaging (MFI).

In light obscuration method, a solution is placed between an optical beam (e.g. generated by a light source such as a laser diode with a wavelength of 680 nm) and a detector. Thus, when a particle transits the measurement zone, it obscures the optical beam and creates a shadow which results in a change in signal strength at the detector.

This signal change is then equated to a particle's equivalent spherical diameter based on a calibration curve created using polystyrene spheres of a known size.

Devices based on this technique are sold under the brand HIAC by Hach Lange, for example.

To provide good accuracy, the method has to be implemented with a large volume of solution (more than 3 ml, which is greater than the volume of a single 1 ml syringe), which implies that it does not allow analyzing containers one by one.

Therefore, several containers have to be flushed in an intermediate larger container (e.g. a beaker) and the content of said intermediate container is then analyzed by the light obscuration device.

The fluid used to carry out the particles level measurement is 0.02% Polysorbate 80 dissolved in Polyphosphate buffer (PBS).

The protocol is the following.

The HIAC equipment is first cleaned with a mixture of WFI and isopropanol alcohol (50/50 proportion), then with WFI only.

All the glassware (intermediate containers for flushing the content of the containers that have to be tested) is also cleaned with WFI, so that the number of particles having a size of 10 µm is of less than 1 particle/ml.

Between each run, a blank with WFI is launched so as to check cell probe and glassware cleanliness.

Then the pharmacopeia norms are conducted on the 0.02% Polysorbate 80—PBS solution flushed from the containers. This means that the stopper is moved towards the distal direction in order to eject the filling solution through the tip of the container into the intermediate container.

The program consists of four runs of 3 ml with the first run discarded, with 3 more ml in order to avoid air bubbles.

In the case of 1 ml injection device, 15 devices are flushed to a common intermediate container in order to obtain the required analysis volume.

On the other hand, MFI is a flow microscopic technology which operates by capturing images of suspended particles in a flowing stream.

Different magnification set-points are available to suit the desired size range and image quality.

The images are used to build a particle database including count, size, transparency and shape parameters.

Said database can be interrogated to produce particle size distributions and isolate sub-populations using any measured parameter.

Suitable variety of equipment is for example sold by Brightwell Technologies (e.g. MFI DPA4200).

The solution is pumped from the tip of the container and goes through a flow cell.

A camera acquires several pictures of a small zone of the flow cell with a known frame rate. On each picture, pixel contrast differences with calibrated background mean that there is a particle. The particle is then digitally imaged.

Due to the particles imaging, the advantage of this method is that it allows making the difference between an air bubble and a silicone oil droplet.

The protocol is the following.

First, flow cell integrity is checked to ensure that the measures will be precise.

Then the cleanliness of the flow cell and the tubing is controlled by a blank with WFI (the particle number has to be below 100 particles/ml).

A run with certified beads (e.g. with a size of 5 or 10 µm and with a concentration of 3000 particles/ml) may be carried out.

The measurement program usually consists of 0.5 ml runs separated by 0.2 ml purge.

In this case, and unlike the analysis protocol used for Light Obscuration method, several syringes are not flushed to a common intermediate container.

Instead, the stopper of each medical injection device to analyze is removed and 0.5 ml of solution is pipetted from the container to the equipment.

FIG. 3 shows that the number of sub visible particles significantly increases when the method involves flushing the container with the solution (i.e. with the light obscuration method described above).

This effect is considered to originate from the fact that when the stopper is actuated, pressure loss due to a difference between the diameter of the barrel and the diameter of the tip is generated, thereby creating turbulence in the region extending distally from the distal end of the barrel. Said turbulence tends to push the lubricant concentrated into the tip and/or to extract lubricant deposited into the tip under the form of particles and to release them into the solution.

In the above mentioned case where a change in the lubricant coating deposition process generates a strong increase in the sub visible particles level, it appears that the modified process tends to deposit more lubricant in the region extending distally from the distal end of the barrel than the previous one.

In order to avoid or at least minimize generation of sub visible particles due to turbulence occurring in the region extending distally from the distal end of the barrel, embodiments of the invention provide controlling the deposition of the lubricant in the barrel, in order to create a lubricant oil coating only on the inner walls of the barrel while preventing lubricant from being deposited in region extending distally from the distal end of the barrel, in particular in the dead space, implantation channel and/or needle inner space of the medical injection device.

Based on the observations described above, the Applicant has determined a correlation between the number of particles greater than 10 µm after flushing and the amount of silicone in region extending distally from the distal end of the barrel.

Figure 4:
FIG. 4 is a graph correlating the number per ml of particles greater than 10 µm after flushing (ordinate) and the silicone quantity in the dead space, the implantation channel and/or the needle inner space (in µg) (abscissa).

FIG. 4 is a graph illustrating this correlation.

To build this graph, the syringe tip/dead space region was separated from the syringe by cutting the glass thanks to a diamond saw. The silicone content on the tip section was extracted thanks to Methyl Ethyl Butyl Ketone and quantified by Atomic Absorption Spectrometry. FIG. 4 presents a correlation between the silicone content in the tip/dead space section and the quantity of sub visible particles >10 µm measured after flushing and quantification by light obscuration, following the protocol described with reference to FIG. 3. Silicone quantity present in the tip/dead space section is linked with the increase in sub visible particles observed after flushing.

Based on FIG. 4, an upper limit for the total amount of silicone in the region extending distally from the distal end of the barrel, e.g. in the dead space, the implantation channel and, if applicable, the needle inner space, that is between 10 and 25 µg, more preferably about 20 µg, is considered to be acceptable. With such an upper limit, the amount of particles greater than 10 µm is about 4 times lower than the worst case of FIG. 3.

What is claimed is:

1. A medical injection device comprising:
   a container intended to contain a pharmaceutical composition, wherein the container comprises:
   a cylindrical barrel, the cylindrical barrel comprising:
   a cylindrical inner wall;
   a proximal end;
   a distal end; and
   a stopper in sliding engagement within the barrel;
   a tapered wall extending distally from the distal end of the cylindrical barrel,
   wherein a junction between the cylindrical inner wall of the barrel and the tapered wall defines the distal end of the barrel;
   a lubricant coating on the cylindrical inner wall of the barrel, wherein the lubricant coating is intended to be in contact with the pharmaceutical composition;
   a tip connected to the tapered wall, wherein the tip comprises an implantation channel;
   a hollow needle inserted in the implantation channel; and
   a region extending distally from the distal end of the cylindrical barrel which is not accessible to the stopper, the region extending distally from the distal end of the cylindrical barrel comprising:
   the implantation channel;
   a dead space surrounded by the tapered wall which is not accessible by the stopper; and
   an inner space of the hollow needle,
   wherein the implantation channel extends between a distal end of the tip and the dead space;
   wherein the lubricant coating is on the cylindrical inner wall of the barrel until a junction of the cylindrical inner wall with the dead space, and
   wherein a total amount of the lubricant in the region extending distally from the distal end of the barrel comprising the implantation channel, the dead space, and the inner space of the hollow needle is less than 25 µg.

2. The medical injection device of claim 1, wherein the total amount of the lubricant in the region extending distally from the distal end of the barrel comprising the dead space, the implantation channel, and the inner space of the hollow needle is less than 20 µg.

3. The medical injection device of claim 1, further comprising a pharmaceutical composition in contact with the lubricant coating in the barrel.

* * * * *